(12) United States Patent
Weissman et al.

(10) Patent No.: US 7,781,179 B2
(45) Date of Patent: Aug. 24, 2010

(54) IDENTIFICATION AND ISOLATION OF TRANSITIONAL CELL CARCINOMA STEM CELLS

(75) Inventors: Irving L. Weissman, Stanford, CA (US); Keith S. Chan, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 12/001,005

(22) Filed: Dec. 7, 2007

(65) Prior Publication Data

US 2008/0182278 A1   Jul. 31, 2008

Related U.S. Application Data

(60) Provisional application No. 60/873,722, filed on Dec. 7, 2006.

(51) Int. Cl.
*G01N 33/53* (2006.01)
*G01N 33/574* (2006.01)
*C12Q 1/00* (2006.01)

(52) U.S. Cl. .................... 435/7.1; 435/4; 435/7.23
(58) Field of Classification Search .............. 435/7.1, 435/4, 7.23
See application file for complete search history.

(56) References Cited

U.S. PATENT DOCUMENTS

2008/0064049 A1*  3/2008  Clarke et al. ........... 435/7.23

OTHER PUBLICATIONS

Dargent et al., Cytokeratin expression by CD34 positive blasts in a case of refractory anaemia with excess of blasts in transformation (RAEB-t), J Clin Pathol 2001; 54:735-736.*
Lapidot et al., A cell initiating human acute myeloid leukaemia after transplantation into SCID miceNature 367, 645-648 (Feb. 17, 1994).*
Brabletz et al., nvasion and Metastasis in Colorectal Cancer: Epithelial-Mesenchymal Transition, Mesenchymal-Epithelial Transition, Stem Cells and -Catenin .Cells Tissues Organs 2005;179:56-65.*
Al-Hajj et al., "Prospective identification of tumorigenic breast cancer cells," Proc. Natl. Acad. Sci. USA, 2003, 100 (7):3983-3988.
Lessard et al., "Bmi-1 determines the proliferative capacity of normal and leukaemic stem cells," Nature, 2003, 423 (6937):255-260.
Li et al., "Identification of pancreatic cancer stem cells," Cancer Res., 2007, 67(3):1030-1037.
Molofsky et al., "Bmi-1 dependence distinguishes neural stem cell self-renewal from progenitor proliferation," Nature, 2003, 425(6961):962-967.
O'Brien et al., "A human colon cancer cell capable of initiating tumour growth in immunodeficient mice," Nature, 2007, 445(7123):106-110.
Pardal et al., "Applying the principles of stem-cell biology to cancer," Nat. Rev. Cancer, 2003, 3(12):895-902.
Park et al., "Bmi-1 is required for maintenance of adult self-renewing haematopoietic stem cells," Nature, 2003, 423 (6937):302-305.
Park et al., "Bmi1, stem cells, and senescence regulation," J Clin. Invest., 2004, 113(2):175-179.
Phillips et al., "The response of CD24(-/low)/CD44+ breast cancer-initiating cells to radiation," J Natl. Cancer Inst., 2006, 98(24):1777-1785.
Reya et al., "Stem cells, cancer, and cancer stem cells," Nature, 2001, 414(6859):105-111.
Ricci-Vitiani et al., "Identification and expansion of human colon-cancer-initiating cells," 2007, Nature, 445 (7123):111-115.
Valk-Lingbeek et al., "Stem cells and cancer; the polycomb connection," Cell, 2004, 118(4):409-418.

* cited by examiner

*Primary Examiner*—Maria Leavitt
(74) *Attorney, Agent, or Firm*—Boziceic, Field & Francis LLP; Pamela J. Sherwood

(57) ABSTRACT

Transitional cell carcinoma stem cells (TCCSC) are identified. The cells can be prospectively isolated or identified from primary tumor samples, and are shown to possess the unique properties of cancer stem cells in functional assays for cancer stem cell self-renewal and differentiation, and in cancer diagnosis.

8 Claims, 9 Drawing Sheets

(8 of 9 Drawing Sheet(s) Filed in Color)

Figure 1. Prospective identification of a rare population of CD44 positive tumor cells in patient transitional cell carcinomas by flow cytometry.
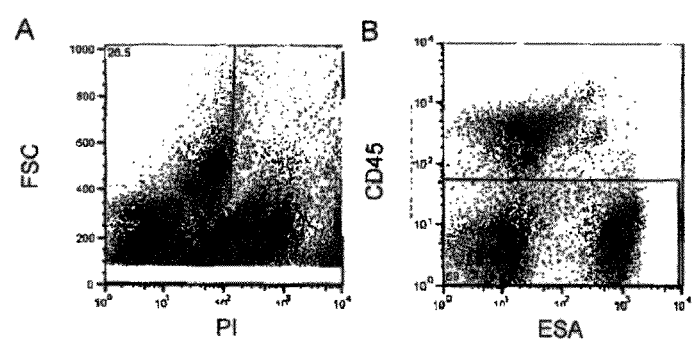

Figure 2. Development of orthotopic and ectopic xenograft models for human transitional cell carcinoma.
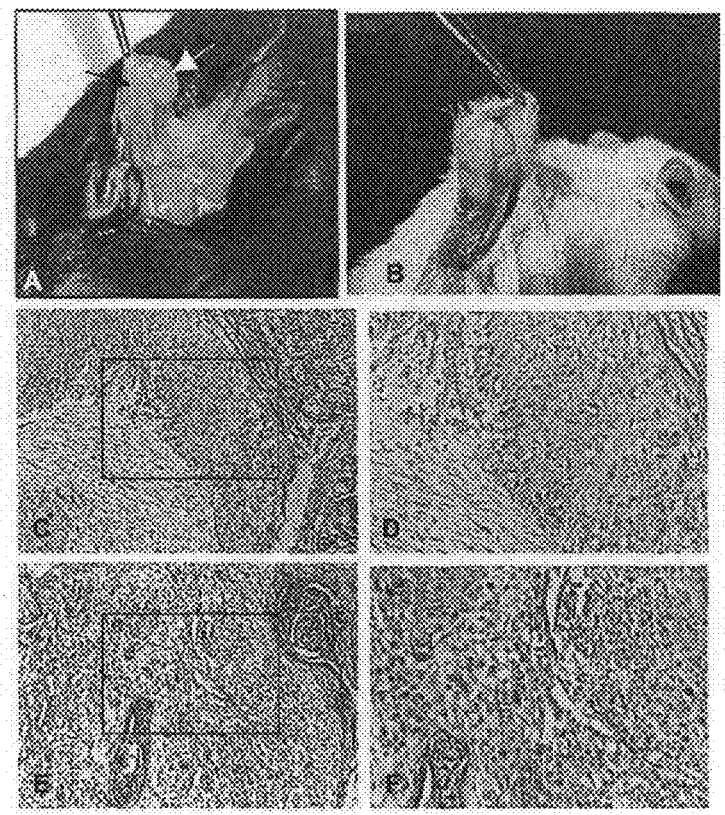

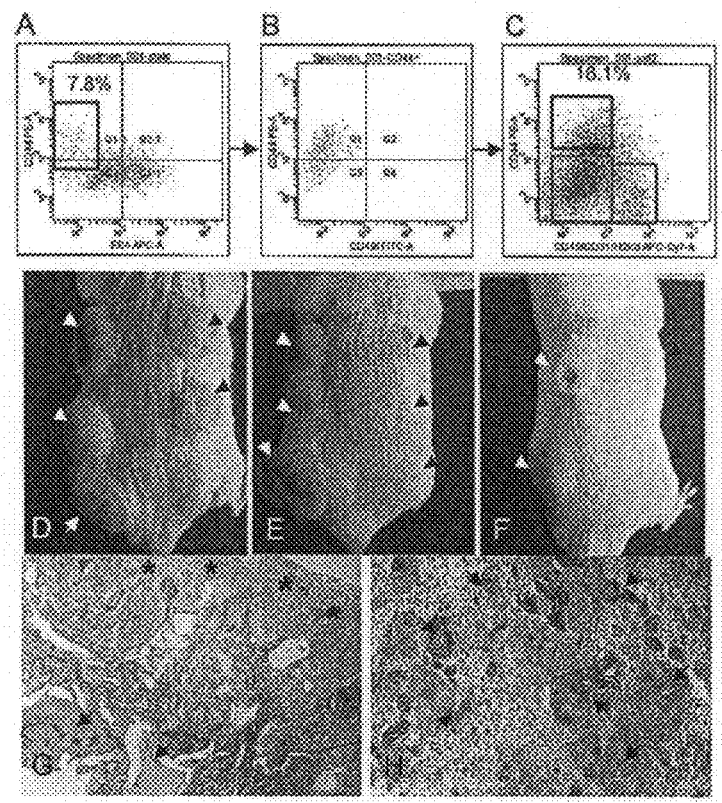
Figure 3. CD44 positive TCC tumor cells exhibit unique properties of CSC: enrichment for tumor-initiating potential, self-renewal and differentiation.

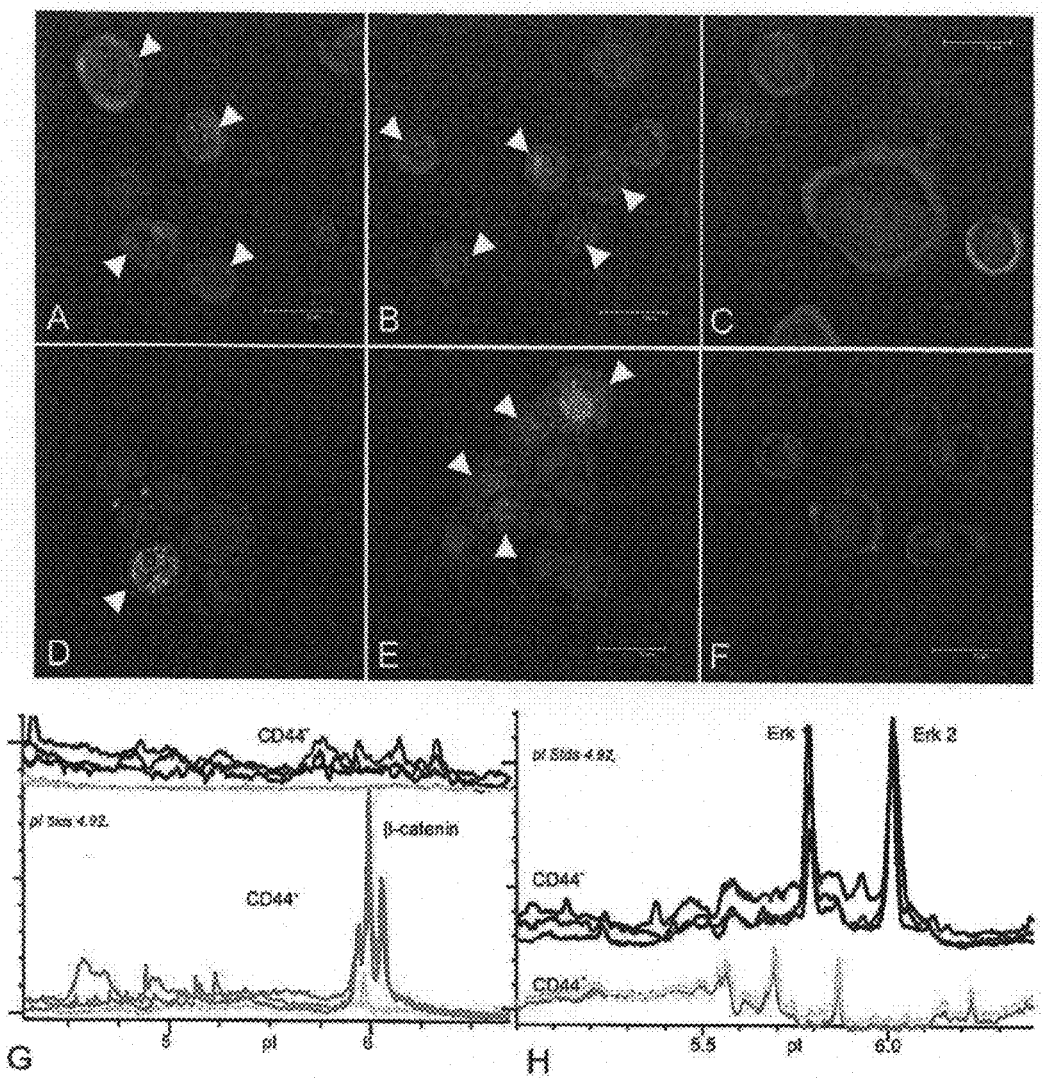

Nuclear beta-catenin in migrating TCC cells
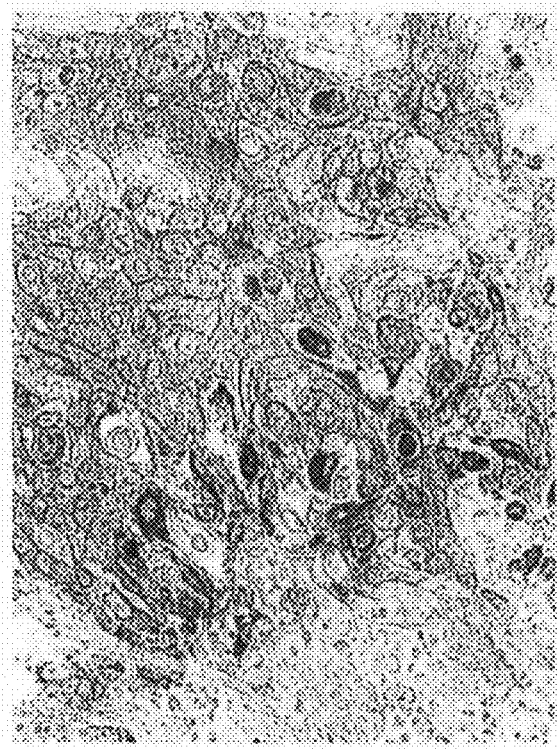
FIGURE 5B

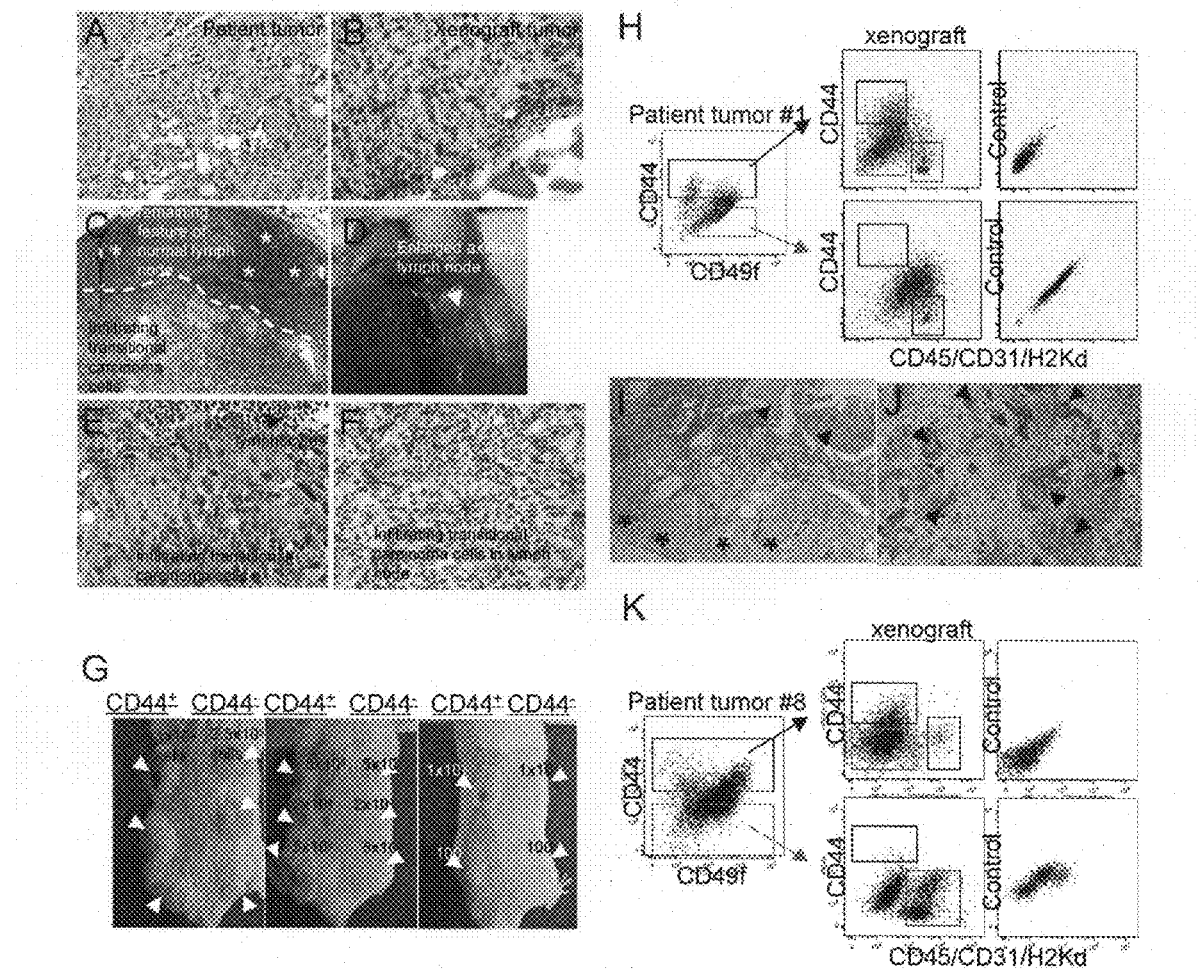

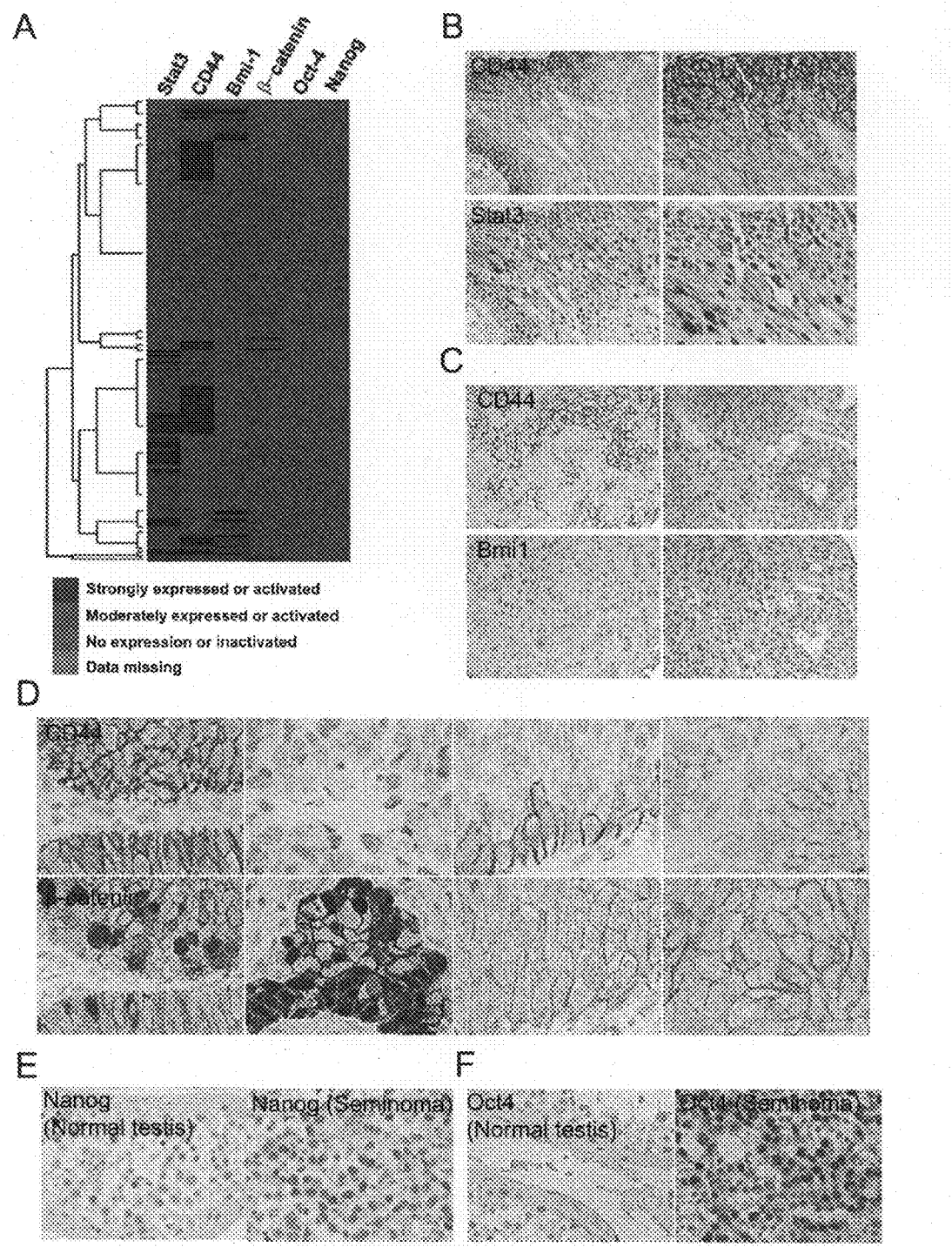

IDENTIFICATION AND ISOLATION OF TRANSITIONAL CELL CARCINOMA STEM CELLS

BACKGROUND OF THE INVENTION

Bladder cancer is the second most common urological malignancy in the United States, which accounts for approximately 13,000 deaths and new cases per year. Ninety percent of bladder malignancies are classified as transitional cell carcinomas (TCCs), which originate from the transitional urothelium that is composed of 3-6 layers thick of basal, intermediate and multinucleate umbrella cells. Seventy percent of tumors are low grade non-invasive papillary lesions at diagnosis, which commonly recur, only 15-20% of which progress into muscle invasive disease. On the other hand, ~30% of TCCs are muscle invasive at diagnosis. Fifty percent of patients with invasive TCCs die from metastasis within 2 years, and the 5-year survival-rate for metastatic bladder cancer is only 6%.

It has long been observed that patient bladder tumors contain intratumoral heterogeneity, consisting of tumor cells with diverse histological morphologies and distinct biological properties. Primary bladder tumor cells possess differential ability for anchorage independent growth, a property defining the transforming ability of cancer cells. This is supported by evidence that only ~0.7% of primary bladder tumor cells have the ability to form colonies in the classical two-layered soft-agar assay, which assays for anchorage independent growth properties of tumor cells. In addition, bladder tumor cells demonstrate diverse proliferation and differentiation status, mostly supported by histological analysis showing distinct staining patterns of proliferation markers (i.e. Ki67 and PCNA) and keratin markers defining differentiation status (i.e. K5/14, K8 and K20).

Basic cancer research has focused on identifying the genetic changes that lead to cancer. This has led to major advances in our understanding of the molecular and biochemical pathways that are involved in tumorigenesis and malignant transformation. However, our understanding of the cellular biology has lagged. A large body of literature has examined the effects of particular mutations on the proliferation and survival of model cells, such as cell lines, fibroblasts and most recently in primary epithelial cells; however, the target cell accumulating actual mutations remained to be elucidated.

A tumor can be viewed as an aberrant organ initiated by a tumorigenic cancer cell that acquired the capacity for indefinite proliferation through accumulated mutations. In this view of a tumor as an abnormal organ, the principles of normal stem cell biology can be applied to better understand how tumors develop. Many observations suggest that analogies between normal stem cells and tumorigenic cells are appropriate. Both normal stem cells and tumorigenic cells have extensive proliferative potential and the ability to give rise to new (normal or abnormal) tissues. Both tumors and normal tissues are composed of heterogeneous combinations of cells, with different phenotypic characteristics and different proliferative potentials.

Because most tumors have a clonal origin, the original tumorigenic cancer cell gives rise to phenotypically diverse progeny, including cancer cells with indefinite proliferative potential, as well as cancer cells with limited or no proliferative potential. This suggests that tumorigenic cancer cells undergo processes that are analogous to the self-renewal and differentiation of normal stem cells. Tumorigenic cells can be thought of as cancer stem cells that undergo an aberrant and poorly regulated process of organogenesis analogous to what normal stem cells do. Although some of the heterogeneity in tumors arises as a result of continuing mutagenesis, it is likely that heterogeneity also arises through the aberrant differentiation of cancer cells.

It is well documented that many types of tumors contain cancer cells with heterogeneous phenotypes, reflecting aspects of the differentiation that normally occurs in the tissues from which the tumors arise. The variable expression of normal differentiation markers by cancer cells in a tumor suggests that some of the heterogeneity in tumors arises as a result of the anomalous differentiation of tumor cells. Examples of this include the variable expression of myeloid markers in chronic myeloid leukaemia, the variable expression of neuronal markers within peripheral neurectodermal tumors, the variable expression of milk proteins or the estrogen receptor within breast cancer, and the differential expression of cytokeratins in a wide spectrum of epithelial tumors including bladder cancer.

It was first extensively documented in acute myeloid leukaemia that only a small subset of cancer cells is responsible for the tumor-initiating potential and maintain the ability to self-renew. Because the differences in clonogenicity among the leukemia cells mirrored the differences in clonogenicity among normal hematopoietic cells, the clonogenic leukemic cells were described as leukemic stem cells. It has also been shown for solid cancers that the cells are phenotypically heterogeneous and that only a small proportion of cells are tumorigenic and can self-renew in vivo. Just as in the context of leukemic stem cells, these observations led to the hypothesis that only rare cancer stem cells exist in epithelial tumors.

In support of this hypothesis, recent studies have shown that, similar to leukemia and other hematologic malignancies, tumorigenic and non-tumorigenic populations of breast cancer cells can be isolated based on their expression of cell surface markers. In many cases of breast cancer, only a small subpopulation of cells had the ability to form new tumors. This work strongly supports the existence of CSC in breast cancer. Further evidence for the existence of cancer stem cells occurring in solid tumors has been found in central nervous system (CNS) malignancies. Using culture techniques similar to those used to culture normal neuronal stem cells it has been shown that neuronal CNS malignancies contain a small population of cancer cells that are clonogenic in vitro and initiate tumors in vivo, while the remaining cells in the tumor do not have these properties.

Stem cells are defined as cells that have the ability to perpetuate themselves through self-renewal and to generate mature cells of a particular tissue through differentiation. In most tissues, stem cells are rare. As a result, stem cells must be identified prospectively and purified carefully in order to study their properties. Perhaps the most important and useful property of stem cells is that of self-renewal. Through this property, striking parallels can be found between stem cells and cancer cells: tumors may often originate from the transformation of normal stem cells, similar signaling pathways may regulate self-renewal in stem cells and cancer cells, and cancers may comprise rare cells with indefinite potential for self-renewal that drive tumorigenesis.

The presence of cancer stem cells has profound implications for cancer therapy. At present, all of the phenotypically diverse cancer cells in a tumor are treated as though they have unlimited proliferative potential and can acquire the ability to metastasize. For many years, however, it has been recognized that small numbers of disseminated cancer cells can be detected at sites distant from primary tumors in patients that never manifest metastatic disease. One possibility is that immune surveillance is highly effective at killing disseminated cancer cells before they can form a detectable tumor. Another possibility is that most cancer cells lack the ability to form a new tumor such, that only the dissemination of rare cancer stem cells can lead to metastatic disease. If so, the goal of therapy must be to identify and kill this cancer stem cell population.

The prospective identification and isolation of cancer stem cells will allow more efficient identification of diagnostic markers and therapeutic targets expressed by the stem cells. Existing therapies have been developed largely against the bulk population of tumor cells, because the therapies are identified by their ability to shrink the tumor mass. However, because most cells within a cancer have limited proliferative potential, an ability to shrink a tumor mainly reflects an ability to kill these cells. Therapies that are more specifically directed against cancer stem cells may result in more durable responses and cures of metastatic tumors.

Epithelial tumors contain a mixed population of cancer cells. It has been hypothesized that functional heterogeneity rather than cellular heterogeneity may account for the fact that not all of the cancer cells in solid tumors have a similar ability to drive tumor formation. Mortality from these diseases remains high due to the development of distant metastasis and the emergence of therapy resistant local and regional recurrences. It is therefore essential that we develop a deeper understanding of the biology of this disease in order to develop more effective therapies.

Cancer stem cells are discussed in, for example, Pardal et al. (2003) Nat Rev Cancer 3, 895-902; Reya et al. (2001) Nature 414, 105-11; Bonnet & Dick (1997) Nat Med 3, 730-7; Al-Hajj et al. (2003) Proc Natl Acad Sci USA 100, 3983-8; Dontu et al. (2004) Breast Cancer Res 6, R605-15; Singh et al. (2004) Nature 432, 396-401.

SUMMARY OF THE INVENTION

Transitional cell carcinoma stem cells (TCCSC) are identified herein. The cells can be prospectively isolated or identified from primary tumor samples, and are shown to possess the unique properties of cancer stem cells in functional assays for tumor initiation, cancer stem cell self-renewal and differentiation. In addition, cancer stem cells can be used as a predictor for disease progression. The TCCSC have the phenotype of being positive for expression of CD44, and retain cytokeratin markers and cellular morphology similar to normal urothelial basal cells, expressing CK5, but not CK20.

Molecular profiling of the TCCSC shows a heterogeneity of self-renewal pathways, where the cells may differentially show increased nuclear localization of one or more of β-catenin; Stat3; or Bmi-1 relative to a normal counterpart cell. These data revealed significant clinical implications, that different subgroup of TCC patients can respond to drugs that target different sets of signaling pathways. In some embodiments of the invention, the TCCSC are classified according to self-renewal pathway, which classification is useful in drug screening, and in developing a course of therapy suitable for the patient.

In some embodiments of the invention, methods are provided for classification or clinical staging of transitional cell carcinomas according to the stem cells that are present in the carcinoma, where greater numbers of stem cells are indicative of a more aggressive cancer phenotype. Staging is useful for prognosis and treatment. In some embodiments, a tumor sample is analyzed by histochemistry, including immunohistochemistry, in situ hybridization, and the like, for the presence of cells that co-express CD44 at the cell membrane and nuclear localization of one or more of β-catenin; Stat3; or Bmi-1. The presence of such cells indicates the presence of TCCSC, and allows the definition of cancer stem cell domains in the primary tumor, as well as cells in lymph node or distant metastases.

In another embodiment of the invention, compositions of isolated TCCSC are provided. The cells are useful for experimental evaluation, and as a source of lineage and cell specific products, including mRNA species useful in identifying genes specifically expressed in these cells, and as targets for the discovery of factors or molecules that can affect them. TCCSC may be used, for example, in a method of screening a compound for an effect on the cells. This involves combining the compound with the cell population of the invention, and then determining any modulatory effect resulting from the compound. This may include examination of the cells for viability, toxicity, metabolic change, or an effect on cell function. The phenotype of TCCSC described herein provides a means of predicting disease progression, relapse, and development of drug resistance. Methods are also provided for administration of therapeutic agents that target cancer stem cells. Identifying TCCSCs by phenotype and signaling pathways unique to them provides a more specific target than conventional therapies.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1. Prospective identification of a rare population of CD44 positive tumor cells in patient transitional cell carcinomas by flow cytometry. (A) FACS plot showing forward scatter versus viable cells as labeled by PI staining. (B) FACS plot showing the exclusion of intra-tumoral hematopoietic cells by the cell surface marker CD45.

FIG. 2. Development of orthotopic and ectopic xenograft models for human transitional cell carcinoma. (A) Injection of at least $1 \times 10^6$ unfractionated patient bladder tumor cells in the bladder wall of Rag2; gamma chain double knock out mice; white arrow indicate engraftment site of xenograft tumor, black arrow indicate the location of mouse bladder. (B) Engraftment of patient bladder tumor cells in the dermal compartment of Rag2; gamma chain double knock out mice. (C and D) Hematoxylin and Eosin staining of patient tumor reveals transitional cell histology with squamous differentiation; black square in C indicates the area of patient tumor magnified in a higher power as shown in D. (E and F) Hematoxylin and Eosin staining of xenograft tumor isolated from immunocompromised mice revealing similar histology to original patient tumor shown in C and D; black square in E indicates the area of xenograft tumor magnified in a higher power as shown in F.

FIG. 3. CD44 positive TCC tumor cells exhibit unique properties of CSC: enrichment for tumor-initiating potential, self-renewal and differentiation. (A) Analysis of primary patient TCC cells on the expression of the cell surface receptor CD44 by flow cytometry (population indicated in black box). (B) Flow cytometry analysis showing the purity of CD44+ tumor cell population after sort. (C) Analysis of TCC xenograft tumor cell on the expression of CD44+ (population indicated in black box) and lineage markers (mouse. CD45, CD31 and H2 Kd antibodies). (D, E and F) Representative photographs showing the dorsal side of immunocompromised mice that were incubated with different doses of tumor cell subpopulations (white arrows indicate injection sites where CD44+ tumor cells were incubated; blue arrows indicate injection sites where CD44− tumor cells were incubated). (G) H&E staining of a xenograft tumor formed from the CD44+ tumor cell fraction. (H) H&E staining of a xenograft tumor formed from the CD44− tumor cell fraction.

FIG. 4. Molecular analysis of β-catenin and the MAP kinase signaling pathways in CD44 positive and CD44 negative tumor cells. (A and B) Representative confocal microscopic images of unphosphorylated β-catenin (Red) in CD44 positive tumor cells from patient bladder tumor. Blue color indicates DAPI nuclear staining. White arrow indicates tumor cells with nuclear localization or activated form of β-catenin. (C) Confocal microscopic images of unphosphorylated β-catenin (Red) in CD44 negative tumor cells from the same patient bladder tumor. Blue arrow indicates a large multinucleate cell with umbrella cell morphology (differentiated cell in urothelium). (D and E) Representative confocal microscopic images of unphosphorylated β-catenin (Green) in CD44 positive tumor cells from serially transplanted xenograft tumor. Blue color indicates DAPI nuclear staining. White arrow indicates tumor cells with nuclear localization or activated form of β-catenin. (F) Confocal microscopic images of unphosphorylated β-catenin (Green) in CD44 negative tumor cells from the same xenograft tumor. (G) Microfluidics western analysis of β-catenin protein level from CD44 positive (Red) and CD44 negative (Black) tumor cells from patient bladder tumor. The sizes of peak indicate the relative protein levels. (H) Microfluidics western analysis of MAP kinase signaling (Erk1 and Erk2-protein level) from CD44 positive (Red) and CD44 negative (Black) tumor cells from the same patient bladder tumor. The sizes of peak indicate the relative protein levels.

FIGS. 5A-5B. (A) Sectional staining of nuclear beta-catenin in subsets of TCC basal cells at the tumor-stromal junction. (B) Nuclear beta-catenin in migrating TCC cells.

FIG. 6. Characteristics and histology of xenograft tumors formed from CD44+ and CD44-bladder TCC subpopulations. (A) Hematoxylin and eosin (H&E) staining of patient tumor #8 (B) H&E staining of xenograft tumor formed from patient #8. (C & E) H&E staining of lymph node from patient #8 that is infiltrated with transitional carcinoma cells. (D) Photograph showing an enlarged axillary lymph node in Rag2/gamma chain double knock out mice that was engrafted with transitional carcinoma cells from patient #8. (F) H&E staining of axillary lymph node from mouse demonstrating similar histology to transitional cells from patient #8. (H & K) Flow cytometry analysis of CD44 expression in two representative patient tumor (#1 & 8) and respective xenograft tumors either formed from a pure patient CD44+ (Black box) or CD44− (Gray box) tumor cell population. Patient CD44+ tumor cells can form xenografts comprising of CD44+ (Black box) and CD44− (Gray Box) tumor cells; while patient CD44− tumor cells only form xenografts comprising of CD44− tumor cells. Blue Box indicates infiltrating mouse cells that are positive for CD45 (hematopoietic cell marker), CD31 (endothelial cell marker) or H2 Kd (mouse major histocompatibility class 1). (G) Photographs showing the engraftment of xenograft tumors in limiting dilution of CD44+ and CD44− tumor cells from patient #1. (I) H&E staining of a representative xenograft tumor formed from patient CD44+ tumor cells (Black Box), comprising areas of less differentiated cells (indicated by *) and areas of terminally differentiated, cells (indicated by arrows). (J) H&E staining of a representative xenograft tumor formed from patient CD44− tumor cells, primarily comprising highly keratinized, terminally differentiated cells (indicated by arrows).

FIG. 8. Immunohistochemical analysis in CD44+ bladder TCCs reveals heterogeneity in pathway activation of oncogenes that are also implicated in self-renewal of stem cells. (A) Illustrated diagram summarizing the relative distribution of CD44 positive bladder TCC specimens in relation to Stat3, Bmi-1, β-catenin, Oct-4 and Nanog. Oct-4 and Nanog are inactive in all bladder TCCs analyzed. (B) Representative immunohistochemical illustrations showing the subgroup of patient specimens coexpressing CD44 and nuclear Stat3 in serial sections; (C) Representative immunohistochemical illustrations showing the subgroup of patient specimens coexpressing CD44 and nuclear Bmi-1 in serial sections; (D) immunohistochemical analysis of CD44 and β-catenin showing different combinations of co-localization. Brown color indicates positive staining and nuclear localization of β-catenin indicates pathway activation; (E & F) Immunohistochemical analysis of Nanog and Oct4 in normal testis and seminoma as positive control (Brown colour indicates positive staining).

DETAILED DESCRIPTION OF THE EMBODIMENTS

Figure 5A:
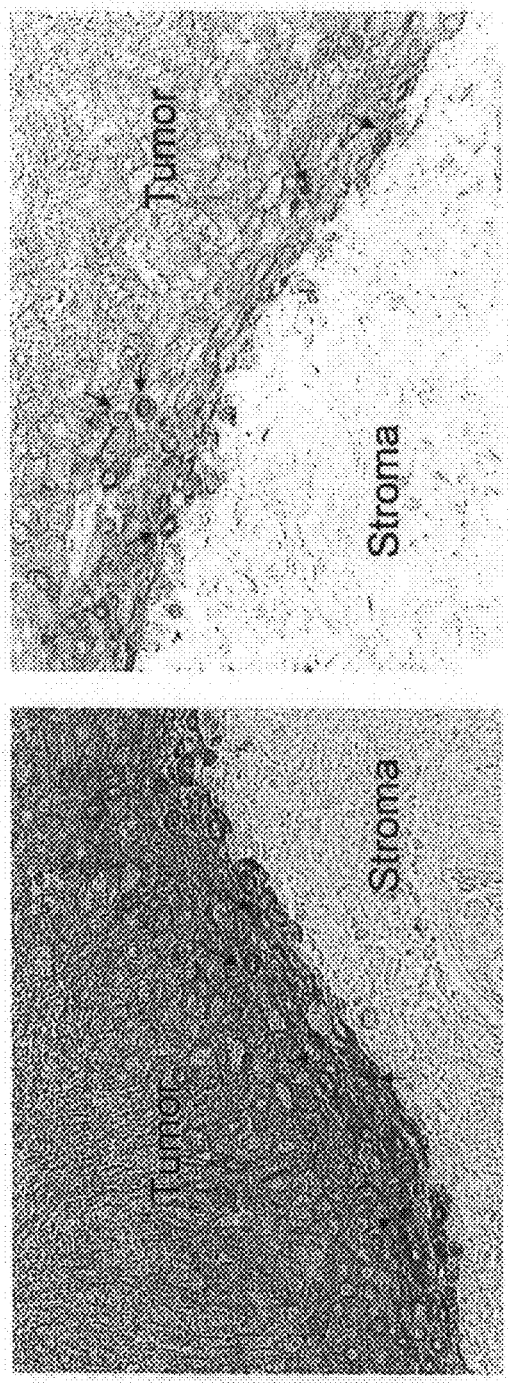

Transitional cell carcinomas are staged by analysis of the presence of cancer stem cells. Staging is useful for prognosis and treatment. In one embodiment of the invention, a cystectomy sample from a transitional cell carcinoma patient is stained with reagents specific for CD44; and optionally a lineage panel. The analysis of staining patterns provides the relative distribution of TCCSC, which distribution predicts the stage of carcinoma. In some embodiments, the cystectomy sample is analyzed by histochemistry, including immunohistochemistry, and the like, for the presence of cells that co-express CD44 at the cell membrane and one or more of β-catenin; Stat3; or Bmi-1 in the nucleus. The cells may also be analyzed for cytokeratin expression, where expression of CK5 is associated with the TCCSC. The presence of such cells indicates the presence of TCCSC, and allows the definition of cancer stem cells in the primary tumor, as well as cells in lymph node or distant metastases. The cells may also be classified according to the specific self-renewal pathway that has been activated.

In one embodiment, the patient sample is compared to a control, or a standard test value. In another embodiment, the patient sample is compared to a pre-carcinoma sample, or to one or more time points through the course of the disease.

Samples, including tissue sections, slides, etc. containing a transitional cell carcinoma tissue, are stained with reagents specific for markers that indicate the presence of cancer stem cells. Samples may be frozen, embedded, present in a tissue microarray, and the like. The reagents, e.g. antibodies, polynucleotide probes, etc. may be detectably labeled, or may be indirectly labeled in the staining procedure. The data provided herein demonstrate that the number and distribution of progenitor cells is diagnostic of the stage of the carcinoma.

The information thus derived is useful in prognosis and diagnosis, including susceptibility to acceleration of disease, status of a diseased state and response to changes in the environment, such as the passage of time, treatment with drugs or other modalities. The cells can also be classified as to their ability to respond to therapeutic agents and treatments, isolated for research purposes, screened for gene expression, and the like. The clinical samples can be further characterized by genetic analysis, proteomics, cell surface staining, or other means, in order to determine the presence of markers that are useful in classification. For example, genetic abnormalities can be causative of disease susceptibility or drug responsiveness, or can be linked to such phenotypes.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims. In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the subject components of the invention that are described in the publications, which components might be used in connection with the presently described invention.

As summarized above, the subject invention is directed to methods of classification of cancers, as well as reagents and kits for use in practicing the subject methods. The methods may also determine an appropriate level of treatment for a particular cancer.

Methods are also provided for optimizing therapy, by first classification, and based on that information, selecting the appropriate therapy, dose, treatment modality, etc. which optimizes the differential between delivery of an anti-proliferative treatment to the undesirable target cells, while minimizing undesirable toxicity. The treatment is optimized by selection for a treatment that minimizes undesirable toxicity, while providing for effective anti-proliferative activity.

The invention finds use in the prevention, treatment, detection or research transitional cell carcinomas. Carcinomas are malignancies that originate in the epithelial tissues. Epithelial cells cover the external surface of the body, line the internal cavities, and form the lining of glandular tissues. In adults, carcinomas are the most common forms of cancer. The urinary bladder is lined by "transitional cells." A transitional cell carcinoma is a tumor of the transitional cell lining of the urinary bladder.

"Diagnosis" as used herein generally includes determination of a subject's susceptibility to a disease or disorder, determination as to whether a subject is presently affected by a disease or disorder, prognosis of a subject affected by a disease or disorder (e.g., identification of pre-metastatic or metastatic cancerous states, stages of cancer, or responsiveness of cancer to therapy), and use of therametrics (e.g., monitoring a subject's condition to provide information as to the effect or efficacy of therapy).

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "individual," "subject," "host," and "patient," used interchangeably herein and refer to any mammalian subject for whom diagnosis, treatment, or therapy is desired, particularly humans. Other subjects may include cattle, dogs, cats, guinea pigs, rabbits, rats, mice, horses, and the like.

A "host cell", as used herein, refers to a microorganism or a eukaryotic cell or cell line cultured as a unicellular entity which can be, or has been, used as a recipient for a recombinant vector or other transfer polynucleotides, and include the progeny of the original cell which has been transfected. It is understood that the progeny of a single cell may not necessarily be completely identical in morphology or in genomic or total DNA complement as the original parent, due to natural, accidental, or deliberate mutation.

The term "normal" as used in the context of "normal cell," is meant to refer to a cell of an untransformed phenotype or exhibiting a morphology of a non-transformed cell of the tissue type being examined.

"Cancerous phenotype" generally refers to any of a variety of biological phenomena that are characteristic of a cancerous cell, which phenomena can vary with the type of cancer. The cancerous phenotype is generally identified by abnormalities in, for example, cell growth or proliferation (e.g., uncontrolled growth or proliferation), regulation of the cell cycle, cell mobility, cell-cell interaction, or metastasis, etc.

"Therapeutic target" generally refers to a gene or gene product that, upon modulation of its activity (e.g., by modulation of expression, biological activity, and the like), can provide for modulation of the cancerous phenotype.

As used throughout, "modulation" is meant to refer to an increase or a decrease in the indicated phenomenon (e.g., modulation of a biological activity refers to an increase in a biological activity or a decrease in a biological activity).

Characterization of Transitional Cell Carcinoma Stem Cells

In transitional cell carcinomas, characterization of cancer stem cells allows for the development of new treatments that are specifically targeted against this critical population of cells, particularly their ability to self-renew, resulting in more effective therapies. "Transitional cell carcinomas", as used herein, refers to the epithelial tumors In human transitional cell carcinomas it is shown herein that there is a subpopulation of tumorigenic cancer cells with both self-renewal and differentiation capacity. These tumorigenic cells are responsible for tumor maintenance, and also give rise to large numbers of abnormally differentiating progeny that are not tumorigenic, thus meeting the criteria of cancer stem cells. All tumorigenic potential was contained within the $CD44^+$ subpopulation of cancer cells, which cells are further associated with CK5 expression and activation of a self-renewal pathway. These cells were able to initiate tumor growth at a dose of from about $10^2$ cells, about $5 \times 10^2$ cells, about $10^3$ cells, providing at least a 100 fold increase in tumor initiating potential compared to the CD44 negative tumor cells.

The TCCSC are identified by their phenotype with respect to particular markers, and/or by their functional phenotype. In some embodiments, the TCCSC are identified and/or isolated by binding to the cell with reagents specific for the markers of interest. The cells to be analyzed may be viable cells, or may be fixed or embedded cells.

In some embodiments, the reagents specific for the markers of interest are antibodies, which may be directly or indirectly labeled. Such antibodies will usually include antibodies specific for CD44; and may include antibodies specific for one or more of β-catenin; Stat3; or Bmi-1.

Transitional Cell Carcinomas

In the US, >60,000 new cases of bladder cancer and about 12,700 deaths occur each year. Bladder cancer is the 4th most common cancer among men and is less common among women; male:female incidence is about 3:1. Bladder cancer is more common among whites than blacks, and incidence increases with age. In >40% of patients, tumors recur at the same or another site in the bladder, particularly if tumors are large, poorly differentiated, or multiple. Expression of tumor gene p53 may be associated with progression.

More than 90% of bladder cancers are transitional cell carcinomas. Most are papillary carcinomas, which tend to be superficial and well-differentiated and to grow outward; sessile tumors are more insidious, tending to invade early and metastasize. Squamous cell carcinoma is less common and usually occurs in patients with parasitic bladder, infestation or chronic mucosal irritation. Adenocarcinoma may occur as a primary tumor but may reflect metastasis from intestinal carcinoma, which should be ruled out. Bladder cancer tends to metastasize to the lymph nodes, lungs, liver, and bone. In the bladder, carcinoma in situ is high grade but noninvasive and usually multifocal; it tends to recur.

Most patients present with unexplained hematuria (gross or microscopic). Some present with anemia, and hematuria is detected during evaluation. Irritative voiding symptoms (dysuria, burning, frequency) and pyuria are also common at presentation. Pelvic pain occurs with advanced cancer, when a pelvic mass may be palpable. Superficial bladder cancer rarely causes death. For patients with deep invasion of the bladder musculature, the 5-yr survival rate is about 50%, but adjuvant chemotherapy may improve these results. Generally, prognosis for patients with progressive or recurrent invasive bladder cancer is poor.

Differential Cell Analysis

The presence of TCCSC in a patient sample can be indicative of the stage of the carcinoma. In addition, detection of TCCSC can be used to monitor response to therapy and to aid in prognosis. The presence of TCCSC can be determined by quantitating the cells having the phenotype of the stem cell. In addition to cell surface phenotyping, it may be useful to quantitate the cells in a sample that have a "stem cell" character, which may be determined by the nuclear localization of one or more of β-catenin; Stat3; or Bmi-1, or by functional criteria, such as the ability to self-renew, to give rise to tumors in vivo, e.g. in a xenograft model, and the like.

Clinical samples for use in the methods of the invention may be obtained from a variety of sources, particularly biopsy samples of transitional cell carincomas from patients, although in some instances samples such as bone marrow, lymph, cerebrospinal fluid, synovial fluid, and the like may be used. For analysis by histology methods, sections, which may be frozen, embedded, etc. are taken from a tumor sample. Once a sample is obtained, it can be used directly, frozen, or maintained in appropriate culture medium for short periods of time. The samples may be obtained by any convenient procedure. Typically the samples will be from human patients, although animal models may find use, e.g. equine, bovine, porcine, canine, feline, rodent, e.g. mice, rats, hamster, primate, etc. In some embodiments, where analysis by flow cytometry is desired, the tissue sample is dissociated, and the cell suspension may be separated by centrifugation, elutriation, density gradient separation, apheresis, affinity selection, panning, FACS, centrifugation with Hypaque, etc. prior to analysis.

The cell sample is contacted with reagents specific for markers that identify TCCSC, as described above. The labeled cells are quantitated as to the expression of cell markers. A number of such methods are known in the art.

The comparison of a differential progenitor analysis obtained from a patient sample, and a reference differential progenitor analysis is accomplished by the use of suitable deduction protocols, AI systems, statistical comparisons, etc. A comparison with a reference tissue analysis from normal cells, cells from similarly diseased tissue, and the like, can provide an indication of the disease staging. A database of reference tissue analyses can be compiled. The methods of the invention provide detection of a predisposition to more aggressive tumor grow growth prior to onset of clinical symptoms, and therefore allow early therapeutic intervention, e.g. initiation of chemotherapy, increase of chemotherapy dose, changing selection of chemotherapeutic drug, and the like.

Cell Staining Methods

Analysis by cell staining may use conventional methods, as known in the art. Techniques providing accurate enumeration include confocal microscopy, fluorescence microscopy, fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide).

The affinity reagents may be specific receptors or ligands for the cell surface molecules indicated above. In addition to antibody reagents, polynucleotide probes specific for an mRNA of interest, peptide-MHC antigen and T cell receptor pairs may be used; peptide ligands and receptor; effector and receptor molecules, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

Of particular interest is the use of antibodies as affinity reagents. Conveniently, these antibodies are conjugated with a label for use in separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

The antibodies are added to cells, and incubated for a period of time sufficient to bind the available antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium that maintains the viability of the cells. A preferred medium is phosphate buffered saline containing from 0.1 to 0.5% BSA. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, etc.

Analysis may be performed based on in situ hybridization analysis, or antibody binding to tissue sections. Such analysis allows identification of histologically distinct cells within a tumor mass, and the identification of genes expressed in such cells. Sections for hybridization may comprise one or multiple solid tumor samples, e.g. using a tissue microarray (see, for example, West and van de Rijn (2006) Histopathology 48(1):22-31; and Montgomery et al. (2005) Appl Immunohistochem Mol. Morphol. 13(1):80-4). Tissue microarrays (TMAs) comprise multiple sections. A selected probe, e.g. antibody specific for a marker of interest; or probe specific for β-catenin, is detectable labeled, and allowed to bind to the tissue section, using methods known in the art. The staining may be combined with other histochemical or immunohistochemical methods. The expression of selected genes in a stromal component of a tumor allows for characterization of the cells according to similarity to a stromal cell correlate of a soft tissue tumor.

The labeled cells are then analyzed as to the expression of cell surface markers as previously described.

TCCSC Compositions

The cells of interest may be separated from a complex mixture of cells by techniques that enrich for cells having the above described characteristics. For isolation of cells from tissue, an appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

Compositions highly enriched for TCCSC are achieved in this manner. The subject population may be at or about 50% or more of the cell composition, and preferably be at or about 75% or more of the cell composition, and may be 90% or more. The desired cells are identified by their surface phenotype, by the ability to self-renew, ability to form tumors, etc. The enriched cell population may be used immediately, or may be frozen at liquid nitrogen temperatures and stored for long periods of time, being thawed and capable of being reused. The cells will usually be stored in 10% DMSO, 50% FCS, 40% RPMI 1640 medium. The population of cells enriched for TCCSC may be used in a variety of screening assays and cultures, as described below.

The enriched TCCSC population may be grown in vitro under various culture conditions. Culture medium may be liquid or semi-solid, e.g. containing agar, methylcellulose, etc. The cell population may be conveniently suspended in an appropriate nutrient medium, such as Iscove's modified DMEM or RPMI-1640, normally supplemented with fetal calf serum (about 5-10%), L-glutamine, a thiol, particularly 2-mercaptoethanol, and antibiotics, e.g. penicillin and streptomycin.

The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. A wide variety of growth factors may be used in culturing the cells, e.g. LIF, steel factor (c-kit ligand), EGF, insulin, IGF, Flk-2 ligand, IL-11, IL-3, GM-CSF, erythropoietin, thrombopoietin, etc In addition to, or instead of growth factors, the subject cells may be grown in a co-culture with fibroblasts, stromal or other feeder layer cells. Stromal cells suitable for use in the growth of hematopoietic cells are known in the art. These include bone marrow stroma as used in "Whitlock-Witte" (Whitlock et al., [1985] *Annu Rev Immunol* 3:213-235) or "Dexter" culture conditions (Dexter et al. [1977] *J Exp Med* 145:1612-1616); and heterogeneous thymic stromal Screening Assays TCCSC are also useful for in vitro assays and screening to detect factors and chemotherapeutic agents that are active on cancer stem cells. Of particular interest are screening assays for agents that are active on human cells. A wide variety of assays may be used for this purpose, including immunoassays for protein binding; determination of cell growth, differentiation and functional activity; production of factors; and the like.

In screening assays for biologically active agents, antiproliferative drugs, etc. the TCCSC composition, usually a culture comprising TCCSC, is contacted with the agent of interest, and the effect of the agent assessed by monitoring output parameters, such as expression of markers, cell viability, and the like. The cells may be freshly isolated, cultured, genetically altered, and the like. The cells may be environmentally induced variants of clonal cultures: e.g. split into independent cultures and grown under distinct conditions, for example with or Without drugs; in the presence or absence of cytokines or combinations thereof. The manner in which cells respond to an agent, particularly a pharmacologic agent, including the timing of responses, is an important reflection of the physiologic state of the cell.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc Characteristically a range of parameter readout values will be obtained for each parameter from a multiplicity of the same assays. Variability is expected and a range of values for each of the set of test parameters will be obtained using standard statistical methods with a common statistical method used to provide single values.

Agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like.

In addition to complex biological agents candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

The term "samples" also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1:1 to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for biological activity by adding the agent to at least one and usually a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents are conveniently, added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of the selected markers. For measuring the amount of a molecule that is present, a convenient method is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) *Trends Biotechnol.* 17(12):477-81). Thus, antibodies can be genetically modified to provide a fluorescent dye as part of their structure. Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999) *Biotechniques* 26(1):112-225; Kawamoto et al., (1999) *Genome Res* 9(12):1305-12; and Chen et al. (1998) *Genomics* 51(3):313-24, for examples.

Kits may be provided, where the kit will comprise staining reagents that are sufficient to differentially identify the TCCSC described herein. A marker combination of interest may include CD44 and a lineage panel as described herein. In other embodiments, a probe or antibody specific for Bmi1 may be included. The staining reagents are preferably antibodies, and may be detectably labeled. Kits may also include tubes, buffers, etc., and instructions for use.

Each publication cited in this specification is hereby incorporated by reference in its entirety for all purposes.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

EXPERIMENTAL

Bladder cancer is the second most common urologic malignancy and is incurable at its advanced stage. Evidence is emerging to support that human tumors contain a rare population of cancer stem cells (CSCs), which are best defined functionally by their unique biological properties, including tumor-initiating potential, self-renewal and differentiation abilities. In the current study, we identify for the first time a CSC population in an advanced stage patient bladder cancer. In 6 out of 8 patient bladder cancers, we identified a rare population of $CD44^+$ tumor cells, comprising ~1-10% of total tumor population. In a xenograft model, as few as 100 $CD44^+$ tumor cells was able to generate tumors, and was at least 200 fold enriched for tumor-initiating potential in a limiting dilution analysis when compared to $CD44^-$ tumor cells. Further, $CD44^+$ tumor cells were able to generate serially transplantable xenograft tumors (indicative of self-renewal) that recapitulate the heterogeneity of original tumor (differentiation) indicated by FACS and histology. Immunofluorescence analysis using confocal microscopy demonstrated nuclear localization of β-catenin, or activation of this self-renewal signaling pathway in ~30-70% of $CD44^+$ tumor cells. In conclusion, these data demonstrate proof of principal for the existence of a tumor-initiating cell population with stem cell-like properties in bladder cancer.

TABLE 1

Frequency of TCC tumor cell engraftment from CD44 positive and negative fractions in immunocompromised mice.

|  |  | $CD44^+$ | $CD44^-$ | unsorted |
|---|---|---|---|---|
| Primary patient tumor | $2.5 \times 10^5$ cells | 1/1 | 0/1 | — |
| Mouse 1$^{st}$ passage | $1.0 \times 10^5$ cells | 2/2 | 1/2 | — |
| Mouse 2$^{nd}$ passage | $5.0 \times 10^6$ cells | — | — | 1/1 |
|  | $1.0 \times 10^6$ cells | — | — | 1/1 |
|  | $5.0 \times 10^5$ cells | — | — | 1/1 |
|  | $2.5 \times 10^5$ cells | — | 3/3 | 1/1 |
|  | $1.0 \times 10^5$ cells | 3/3 | 1/3 | 0/1 |
|  | $5.0 \times 10^4$ cells | 4/4 | 2/4 | — |
|  | $2.0 \times 10^4$ cells | 4/4 | 1/4 | — |
|  | $5.0 \times 10^3$ cells | 4/4 | 0/4 | — |
|  | 1000 cells | 2/4 | 0/4 | — |
|  | 100 cells | 1/4 | 0/4 | — |

Example 2

Molecular Profiling of Patient Bladder Cancers Reveals Heterogeneity in Active Self-Renewing Pathways and the Existence of Unique Tumor-Initiating Cells Bladder cancer is a heterogeneous disease. Enzymatically dissociated patient bladder transitional cell carcinomas (TCCs) formed xenografts in the skin of immunocompromised mice; engraftment success closely correlated with their TNM staging. Through screening bladder TCC suspensions with CD44, CD133, CD24, CD49f, epithelial specific antigen, CD166 and CD105, we found a heterogeneity in the immunophenotype of the TCCs. CD44 was consistently expressed in 13 out of 14 bladder TCCs analyzed as a small subpopulation (3.4 to 36.3%) of total tumor cells. Five out of 13 bladder TCCs engrafted in vivo, and the CD44+ subpopulation consistently enriches for a tumor-initiating population; this CD44+ subset is 10-200 fold more tumorigenic than CD44− cells within the same tumor. We-analyzed a tissue array containing more than 300 bladder TCCs by immunohistochemistry. Approximately 40.4% of TCCs contain CD44+ cells; these cells usually express cytokeratin 5 (CK5) ($P<0.0001$) but not cytokeratin 20 ($P=0.8160$). Further, molecular profiling of CD44+ bladder TCCs focusing on oncogenic pathways that were also implicated in the self-renewal of stem cells (i.e. β-catenin, Bmi-1, Stat3, Oct4 and Nanog) classifies tumors into subgroups. A significant correlation was found between CD44, Bmi-1 and Stat3 in the muscle invasive properties of bladder TCCs ($P=0.0047$). In one TCC, CD44+ tumor-initiaitng cells expressed nuclear, activated β-catenin. These data revealed a heterogeneity in bladder TCCs; rare tumor-initiating cells likely drive tumor development through various oncogenic pathways in different subset of patients.

Results

Establishment of a xenograft model with engraftment ability closely associating with the TNM staging of original patients. We have collected 13 freshly isolated patient bladder TCCs; eleven of which are muscle invasive (pT2 and pT3 stage), one of which is carcinoma in situ and one without disclosed clinical information (Table 2). Tumors were dissociated into viable cell suspensions by enzymatic digestion, and we have tested their relative ability to engraft in an immunocompromised mouse strain that is deficient in recombinase activating gene 2 (RAG2) and the common cytokine receptor γ chain (γc) (RAG2−/γc−). These mice lack of T, B and NK cells and were more efficient in human primary cell engraftment. There was only a 35.7% (5 out of 14) successful tumor take rate with usually three months latency when tumor cells were injected intradermally. Importantly, the relative ability for tumors to engraft in vivo seemed to associate closely with the TNM staging of original patients (Table 2), with 4 out of 6 pT3 stage tumors engrafted, 1 out of 5 pT2 stage tumors engrafted and none engrafted below pTa stage. In a high percentage of mice that were engrafted with human tumors (3 out of 5) immunocompromised mice died early due to pneumocystis pneumonia and/or bacterial bronchopneumonia. Of the two tumors that were serially transplantable in vivo, both were at pT3 stages (Table 2). In particular, original patient tumor #8 with lymph node metastasis (pT3a pN1 pMX) (FIG. 6C) also formed lymph node metastasis after 8 months of engraftment in immunocompromised mice (FIGS. 6D, E & F), with histopathology closely resembling the original patient tumor (FIGS. 6A-F). Histological analysis by hematoxylin and eosin (H&E) staining revealed that xenograft tumors (FIG. 6B) often retain the original histology of patient tumors (FIG. 6A), an important criteria of a xenograft model; suggesting specific subpopulation of patient tumor cells are not being selected in vivo.

Flow cytometry analysis of patient bladder TCCs reveals heterogeneity of immunophenotype. In several types of solid tumors, a unique subpopulation of tumorigenic cells was identified based on their ability to form xenografts in immunocompromised mice. The general approach involved the utilization of flow cytometry to analyze and sub-fractionate patient tumors that were dissociated into cell suspension. In brief, a tumorigenic subpopulation can either be isolated or enriched based on the immunophenotype of tumor cells; for instance, CD44+/CD24−/ESA+ cells from patient breast tumors and pleural effusions, CD133+ tumor cells from glioblastomas and medullobastomas, CD44+ cells from head and neck cancers, CD44+/CD166+ cells from colorectal cancers and CD44+/CD24+/ESA+ cells from pancreatic cancers were demonstrated to contain a tumorigenic subpopulation. Here, we took the lead from these studies and have analyzed 14 freshly isolated bladder TCCs by flow cytometry. Tumor cell suspensions were obtained by enzymatic dissociation; and infiltrating hematopoietic and endothelial cells were excluded based on the expression of CD45 and CD31 respectively. Even with a limited number of stem cell surface markers that we have screened, which included CD44, CD133, CD24, CD49f/integrinα6, ESA, CD166 and CD105, it is clear that individual tumors are very heterogeneous in their immunophenotype. Currently, there are not sufficient specimens being analyzed to define a clear association between relative immunophenotype and various TNM staging. Importantly, one single marker CD44 is consistently expressed in 13 out of 14 bladder tumors being analyzed, comprising an expression frequency from ~3.4% to 36.3% of the total population (Table 2 & 3), while 1 out of 14 specimen did not contain CD44 expression (Table 2).

In vivo human xenograft model reveals a unique tumor-initiating cell population in high grade patient TCCs. Therefore, we decided to focus on this marker and determine whether CD44 expressing bladder tumor cells contain unique biological properties in vivo. To determine the relative tumorigenic potential in vivo compared to other tumor cells within the same tumor, we purified the CD44+ subpopulation by flow cytometry and injected them intradermally into RAG2−/γc− mice. In 5 out of 14 patient TCC specimens, the fractionated CD44+ tumor cell subpopulation engrafted as xenograft, while CD44− cells from the same tumor either do not engraft or require a relatively higher number of CD44− cells to engraft in vivo (Table 3). These data revealed that a CD44+ tumor cell subpopulation enriches for tumor-initiating cells from these 5 bladder TCCs. Further, in two of these engrafted CD44+ xenografts (patient #1 & 8), we found that they were able to generate xenograft tumors upon serial transplantation. In the second serial transplantation, we were able to perform detailed limiting dilution experiment on un-fractionated and fractionated tumor cells. We found that at least $2.5 \times 10^5$ un-fractionated tumor cells were required to generate xenografts (Table 3, patient #1). Further, we found that pure CD44+ tumor cells can form xenografts more effectively than CD44− cells within the same tumor. Remarkably, as few as 100-500 CD44+ tumor cells can form xenografts in vivo (Table 3, patient #1 & 8), suggesting a frequency of at least 1 out of 100-500 CSC was present in CD44+ bladder tumor cells; while at least $2.0\text{-}5.0 \times 10^4$ CD44− tumor cells were necessary to induce xenografts (Table 3, patient #1 & 8). These data clearly suggest that in serially transplanted xenografts, CD44+ bladder tumor cells also contain tumor-initiating cells and were at least 100 to 200-fold enriched for tumor-initiating potential when compared to CD44− cells (Table 3, patient #1 & 8).

CD44 positive tumor cells possess unlimited self-renewing capacity in comparison to CD44 negative tumor cells in pT3 stage bladder cancers. In patient TCC specimens #1 & 8, CD44+ tumor cells were able to generate serially transplantable xenograft tumors in RAG2−/γc− mice. Flow cytometry analysis revealed that xenografts derived from pure patient CD44+ tumor cells (FIGS. 6H & K, Black box) gave rise to a heterogeneous tumor population containing both the basal cell-like CD44+ (FIGS. 6H & K, Black Box) and more differentiated CD44− tumor cells (FIGS. 1H & K, Gray Box). Mouse cells were excluded from the analysis with a cocktail containing antibodies to mouse CD31 (endothelial), CD45 (hematopoietic cell) and H2 Kd (mouse histocompatibility class 1) molecules (FIGS. 6H & K, blue box). Furthermore, H&E staining of xenografts derived from CD44+ tumor cells of patient #1 revealed areas of less differentiated tumor cells (FIG. 6I, area indicated by asterix), as well as terminally differentiated tumor cells with high keratinization (FIG. 6J, area indicated by arrows). On the other hand, in xenografts formed from a relatively higher number of CD44− tumor cells ($2$-$5\times10^4$) from patient #1 (FIG. 6H, Gray Box), flow cytometry revealed that the majority of cells in the tumor were CD44− cells. Histological analysis with H&E staining in these xenograft tumors revealed areas mostly comprised of highly keratinized, terminally differentiated cells (FIG. 6J, area indicated by arrows) with very few cellular components (FIG. 6J). For patient #8, xenografts formed from CD44+ and CD44− tumor cells did not demonstrate a significant difference in histology, revealing pathological differences between individual tumor specimens. Further, xenografts formed from a higher number of CD44− cells ($3.0\times10^5$) reveal immunophenotype mostly comprising of CD44− tumor cells (patient #8, FIG. 1G), importantly, as high as $1\times10^5$ CD44− tumor cells from this xenograft line were not able to generate secondary xenografts upon serial transplantation, indicating a limited self-renewal and/or proliferative capacity of CD44− tumor cells.

Collectively, these data convincingly revealed that CD44+ tumor cells in bladder TCCs contain a "self-renewal" property, which can give rise to basal-cell like CD44+ tumor cells; and retain the ability to "differentiate" into a more differentiated CD44− tumor cell population. Although a higher number of CD44− tumor cells can form xenografts in vivo, their limited self-renewal ability is revealed by their inability to form xenografts upon serial transplantation.

Figure 7:
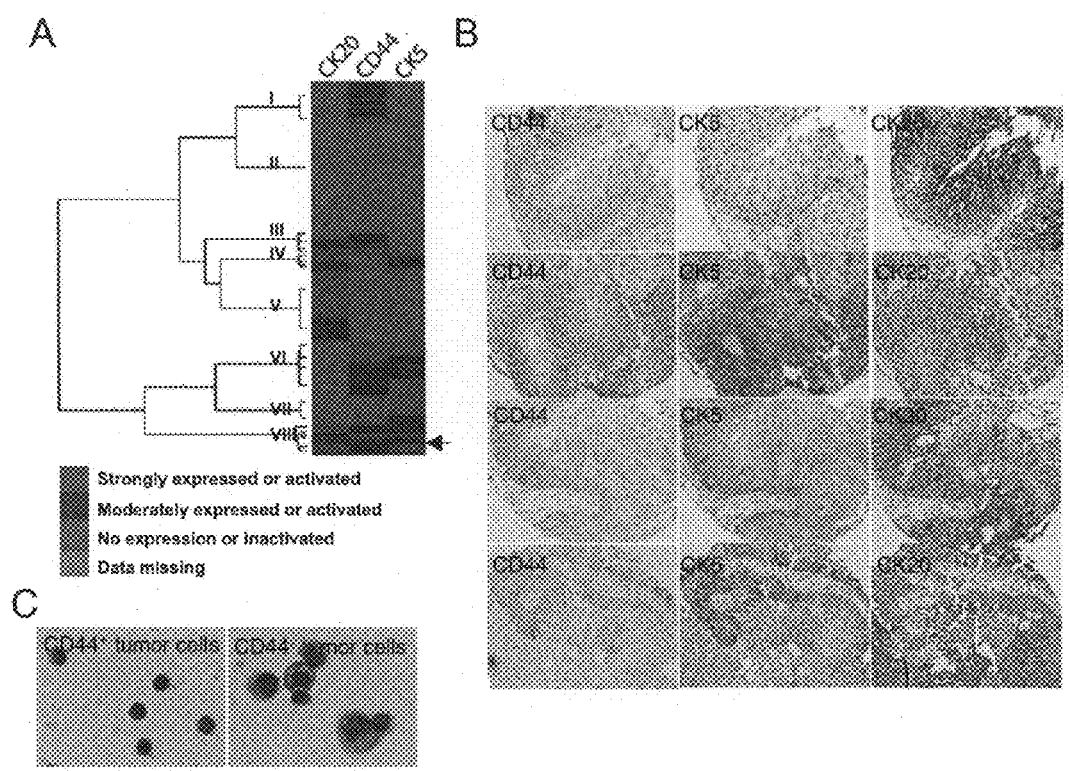
FIG. 7. CD44+ TCC subpopulation retain cytokeratin markers and cellular morphologies resembling normal urothelial basal cells. (A) Illustrated diagram summarizing the relative distribution of CD44, CK5 and CK20 positive bladder TCCs in a bladder cancer tissue array containing ~300 specimens. Red color indicates positive immunohistochemical staining; green indicates negative-staining and grey indicates data that are missing. Arrow indicates the subgroup of bladder TCCs expressing all three markers (i.e. CD44, CK5 and CK20). (B) Immunohistochemical analysis of CD44, cytokeratin 5 (basal cell marker) and cytokeratin 20 (differentiated cell marker) in serial sections of four representative bladder TCCs from group 8 (indicated by arrow), brown color indicates positive staining. (C) Giema-Wright staining showing the cellular morphology of fractionated CD44+ and CD44− tumor cells (patient #3).

CD44 expressing subpopulation in TCC specimens retain cytokeratin expression and cellular morphology and properties resembling that of urothelial basal cells. In normal human bladder urothelium, it was previously reported that CD44 primarily localizes in the basal cell compartment. We are interested to determine whether CD44+ bladder tumor cells retain properties similar to normal urothelial cells with the conventional basal cell marker cytokeratin 5 or differentiated cell marker cytokeratin 20 by immunohistochemistry, in a tissue array containing ~337 bladder TCC specimens. Immunohistochemical data was analyzed and scored based on the percentage of positive expression for each marker within individual tissue section. The bladder TCC specimens were then clustered into subgroups based on the relative expression of CD44, CK5 and CK20. The results were summarized in a colorimetric representation as demonstrated in FIG. 7A. Red represents positive cases, green represents negative cases and grey represents data that are missing. This bladder cancer tissue array contains 84 cases of female and 253 cases of male to a total of 337 patients in a 3:1 male to female ratio. Approximately 59.6% (201 out of 337 cases) of the patient tissue sections stain negative for CD44 (represented in green), and 40.4% (136 out of 337 cases) stain positive for CD44 (represented in red). Importantly, 84.6% of CD44 positive cases either stain positive for CK5 (FIG. 8A, group 6 & 8) or do not stain positive for any cytokeratins (FIG. 8A, group 1). Multivariant regression analysis revealed a statistically significant correlation of CD44 and CK5 ($P<0.0001$) expression, but not with CK20 ($P=0.8160$). In bladder TCCs expressing all three markers, i.e. CD44, CK5 and CK20 (group 8 as indicated by arrow), the CD44 expressing tumor cells often co-localize with CK5 and is mutually exclusive to CK20 in well differentiated, moderately differentiated, as well as more dyplastic lesions (FIG. 7B).

Further, in limited cases of freshly isolated tumors (n=4), we were able to examine the cellular morphology of CD44+ and CD44− cells prepared from cytospin, followed by Giemsa-Wright staining. As shown in FIG. 8C in a representative TCC, CD44+ tumor cells possess a high nuclear to cytoplasmic (NC) ratio (from patient #3). In addition, CD44+ tumor cells were relatively smaller and homogenous in size (FIG. 7C), typical characteristics of basal urothelial cells. On the other hand, CD44− tumor cells were more heterogeneous in size, containing cells with characteristics of moderately and terminally differentiation (FIG. 7C). In other cases, either there weren't significant differences in cellular morphologies between CD44+ and CD44− cells or follow similar morphology of that described in FIG. 7C. Collectively, these data demonstrate that CD44 expressing tumor cells retain cytokeratin markers and cellular morphology similar to normal urothelial basal cells.

Subclassification of bladder TCCs by molecular profiling of CD44 and oncogenic pathways that are implicated in the self-renewal of stem cells. Further, we focused on these 40.4% of CD44 expressing tumor specimens in the bladder cancer tissue array (described in FIG. 7), in attempt to identify signaling molecules that have important clinical implications for this subset of tumors. Certain signaling molecules such β-catenin, Bmi-1, Stat3, Oct-4 and Nanog have been implicated to maintain self-renewal of adult or embryonic stem cells. Interestingly, some of these signaling molecules crucial for the self-renewal of stem cells are also implicated in the tumorigenic process.

Immunohistochemical analysis of these oncoproteins in bladder cancers revealed a heterogeneous molecular profile in pathway activation, which subclassifies bladder cancers into various groups based on the expression of CD44 and the active state of Stat3, Bmi-1, β-catenin, Oct-4 and Nanog (illustrated in FIG. 8A). Red represents positive cases, green represents negative cases and grey represents data that are missing. Within the CD44 expressing bladder cancers, different subsets of tumors seem to utilize either one or more of these oncogenic/self-renewal pathways (FIG. 8A). For instance, 10% of CD44+ tumors (14 out of 140) contain nuclear localization of Bmi-1, 5% of CD44+ contain nuclear localization of β-catenin (7 out of 140), and 45% of CD44+ tumors contain nuclear localization of Stat3 (35 out of 140) (FIG. 8A). Fifteen percent of CD44+ tumors contain activation of two of such oncogenic pathways being analyzed (21 out of 140). Importantly, there is a statistically significant correlation between CD44, Bmi-1 and Stat3 in relation to the invasive properties of bladder cancer ($P=0.0047$). While activation of β-catenin has an association with high grade bladder cancers, it is not statistically significant ($P=0.06$). Careful analysis revealed that although a large fraction of nuclear Stat3 (FIG. 8B) or Bmi-1 (FIG. 8C) positive cells co-localize with CD44+ tumor cells, their expression is not completely restricted CD44+ tumor cells. In contrast, in the relatively small subset of tumor specimens with both CD44 expression and active/nuclear β-catenin, nuclear β-catenin seemed to strictly localize within CD44+ tumor cells (FIG. 8D).

On the other hand, we obtained no positive staining for Oct4 and Nanog in all bladder cancer specimens analyzed (FIG. 8A, indicated in green color); although we were able to obtain strong nuclear staining of Oct-4 (FIG. 8E) and Nanog (FIG. 8F) in patient seminomas as positive control and no background staining in normal testis as negative control (FIGS. 8E & F). These data are in contrast to a recent report that activated or nuclear accumulation of Oct-4 is of high incidence, in 31 out of 32 patient bladder tumors analyzed.

In the current study, we have employed multiple approaches to identify a CD44 positive tumorigenic subpopulation with unlimited self-renewal capacity from bladder TCCs. This unique subpopulation retains cytokeratin markers and cellular morphologies resembling that of urothelial basal cells. Importantly, molecular profiling of CD44 positive bladder cancers revealed heterogeneity of self-renewal pathways. These data implicate that diverse sets of epigenetic and genetic alterations can accumulate in urothelial basal cells from different patients, leading to this molecular heterogeneity that can subclassify bladder TCCs. These data revealed significant clinical implications, that different subgroup of bladder TCC patients may respond to drugs that target different sets of signaling pathways. Therefore, the evaluation of successful therapeutics in current clinical trials based on the response of a major patient population may not be entirely valid, which may overlook agents that target a smaller subgroup of patients. Further, the existence of a tumorigenic subpopulation in bladder cancers suggest that current approaches in molecular profiling of bulk tumor populations may not reveal effective therapeutic targets.

Normal urothelium is a slow cycling epithelium, which turnovers every 6 months to 1 year. However, in response to wounding induced by physical and chemical injury, mouse and rat urothelium can initiate regeneration in as little as 12 hours, peak at 24 hours and completely heal over the wound site in 2-3 days. Further, the urothelium undergoes frequent squamous metaplasia (when one differentiated cell type is replaced by another), especially under a vitamin A deficient diet. This slow cycling urothelium with high regenerative potential and high plasticity of the urothelium support the hypothesis that an adult cell progenitor population exists within the adult bladder. The median age of bladder cancer at diagnosis in the United States is 63, and it is well established that chronic exposure to cigarette smoking or occupational exposure to chemicals such as polycyclic aromatic hydrocarbons (PAH) has an established link to bladder cancer risk. Further, cancer patient who received high dose treatment of the chemotherapeutic agent cyclophosphamide and/or irradiation also has a higher risk in developing bladder cancer. On other hand, chronic inflammation of the bladder caused by a parasite Schistosoma hematobium in the region of Northern Africa also have a risk to the development of squamous cell carcinomas (SCCs) of the bladder, although over 90% of bladder cancers are transitional cell carcinomas.

These evidences led to our hypothesis that there may be a "target cell" population within the normal urothelium, which preferentially accumulate epigenetic and genetic alterations caused by continued physical and chemical assaults from various sources, eventually leading to the loss of tissue homeostasis through extensive cell proliferation, block of differentiation, insensitivity to apoptotic signals and/or genomic instability after a long latency period (~63 years). Our data revealed a CD44+ tumorigenic subpopulation with unlimited self-renewal capacity in bladder TCCs (Table 3 and FIG. 6). This subpopulation retained cytokeratin markers and cellular morphology resembling that of normal urothelial basal cells (FIG. 7), indicating that the basal cell compartment is the "target cell" population for transitional cell carcinoma initiation.

Another important observation extending from the current study is the molecular heterogeneity of bladder TCCs, even from a small screen focusing on oncogenic pathways that are also implicated in the self-renewal of stem cells. This raised the possibility that different subset of bladder TCC patients, although may contain the same "target cell" population for tumor initiation, may indeed accumulate totally diverse set of epigenetic and mutagenic alterations leading to the development of advanced stage disease. In CD44 expressing bladder TCCs, there is a significant correlation between CD44, Bmi-1 and Stat3 in the invasive properties of this disease. Although long term clinical follow up or survival data from this set of patients is currently unavailable, there is reported correlation between the invasive properties of bladder TCCs and poor prognosis, and invasion remained one of the hallmarks for the classification (TNM staging), prognosis, and management of this disease. Our study is the first to reveal the possible role of oncogenic Bmi-1 and Stat3 in the invasive properties of bladder TCCs. Currently, we are collecting patient specimens from such subgroups to evaluate the functional significance of these individual pathways in maintaining the initiation and growth of xenograft tumors in vivo. In conclusion, our current data support the notion that unique tumor-initiating cells with unlimited self-renewal capacity exist in bladder TCCs, which drive tumor development through different oncogenic pathways in diverse subset of patients.

Experimental Procedures

Bladder tumor tissue dissociation. Enrollment of human subjects to the current study has been approved by the Stanford Institutional Review Board under the protocol 1512. Individual consents have been obtained from all subjects. Tumor tissues obtained from cystectomy or xenograft were immediately incubated in calcium free Hanks' Balanced Salt Solution (Invitrogen, N.Y.) With 2% chelexed fetal bovine serum (HBSS/2% FBS). Tumors were disaggregated mechanically with sterile scalpel and minced into 1-2 mm$^3$ pieces, followed by enzymatic digestion in media 199 containing proteolytic (Accumax, Innovative Cell Technologies, Inc.), collagenolytic (200U Type I and 20U Type IV collagenase) (Sigma-Aldrich C-0130, C-5138) and, DNAse enzymes at 37° C. for 2 to 6 hours. Cells were then filtered through a 100 μm nylon mesh and washed once with calcium free HBSS/2% FBS.

Analysis and cell separation by flow cytometry. Tumor cell suspensions were washed with HBSS/2% FBS, incubated with mouse 1 g for 10 min to prevent nonspecific antibody binding, and stained with PE-conjugated anti-CD44 (1:50, BD Pharmingen 550989) antibody for 15 min at 4° C. For patient specimens, a lineage cocktail containing Cy7-PE-conjugated anti-CD45 (1:200, BD Pharmingen 557748) and biotin-conjugated anti-CD31 (1:100, eBioscience 13-0319-82) antibodies were stained for 15 min at 4° C., followed by a wash with HBSS/2% FBS and secondary antibody incubation with Strepavidin-conjugated pacific blue antibody (1:400, Molecular Probes S11222). For xenograft specimens, a lineage cocktail containing biotin-conjugated rat anti-mouse CD45 (1:200, BD Pharmingen 553077), CD31. (1:260, BD Pharmingen 553371) and H2 Kd (1:200, BD Pharmingen 553564) antibodies were stained for 15 min at 4° C., followed by a wash with HBSS/2% FBS and secondary antibody incubation with Strepavidin-conjugated pacific blue antibody. Finally, tumor cell suspensions were resuspended in 1 mg/ml propidium iodide (PI). Flow cytometry analysis and cell sorting was performed on FACSAria (Becton Dickinson) under low pressure setting (20 psi) with a 100 μm nozzle. Data was analyzed using FlowJo software (Tree Star).

Transplantation of tumor cell suspension into immunocompromised mice. Either un-fractionated or fractionated tumor cell suspensions were resuspended in high concentration matrigel (Becton Dickinson 354248). Adult Rag2⁻γc⁻ mice at age of 4-8 weeks were first shaved and anesthetized by 15 μl/g body weight of 2,2,2-Tribromoethanol (Sigma-Aldrich T-48402). Tumor cell suspensions were injected intradermally into the dorsal side of mouse skin by 31 gauge insulin syringes (Becton Dickinson). Tumor formation was monitored on a daily basis.

Immunofluorescence staining and confocal microscopy. Tumor cells were separated by flow cytometry and resuspended in 10 μl of HBSS, placed on Superfrost/Plus slides (Fisher Scientific), and semi-dry for 10-15 min. Cells were surrounded by ImmEdge pen (Vector Laboratories H4000) and fixed with 0.2% paraformaldehyde (Electron Microscopy Sciences 15713-S) for 10 min. Cells were washed once with HBSS, non-specific antibody binding was blocked with 10% goat serum for 15 min, and stained with anti-active-β-catenin antibody (Upstate 05-665 clone 8E7) at a concentration of 1:200 for 30 min. Cells were then washed twice with HBSS and stained with goat anti-mouse AlexaFluor® 594 (1:1000) or goat anti-mouse AlexaFluor® 488 (1:500) secondary antibodies (Molecular Probes) for 30 min. Cells were washed twice with HBSS and slides were mounted with Vectorshield mounting media containing DAPI (Vector Laboratories H-1500). Slides were visualized under the Leica SP2 AOBS confocal laser scanning microscope and images were collected with the Leica Confocal, v 2.5, build 1347 software.

Immunohistochemical analysis in tissue sections. Ten-micron paraffin embedded tissue sections were but, deparaffinized through 3 changes' of xylene 10 min each, and hydrated with, graded ethanol (100% 2×, 95% 2×, 80% 1× and 70% 1× with ddH₂O 2×). Antigen retrieval was performed with 1M EDTA at pH8.0 (for anti-β-catenin) and 10 mM citrate buffer at pH6.0 (all other antibodies) by microwave for 15 min. Slides were cooled for at least 30 min, and staining was performed using the DAKO EnVision kit (K4006 and K4011) following manufacture protocol. Primary antibodies were applied at indicated concentrations, anti-β-catenin (BD Transduction 610154, 1:1000), anti-CD44 (BD Pharmingen 555477, 1:25), anti-Oct-3/4 (Santa Cruz sc-5279, 1:50) and anti-Bmi-1 (AbCam 14389-25, 1:100). Slides were then counterstained with hematoxylin, dehydrated with graded ethanol (95% 2×, 100% 3×), cleared by xylene and mounted in Protex mounting media. Five-micron frozen sections were stained with the same protocol without going through the antigen retrieval step.

What is claimed is:

1. A method for characterizing a transitional cell carcinoma (TCC) from a patient, the method comprising:
    contacting a sample of said transitional cell carcinoma with reagents specific for CD44 and specific for CK5;
    quantitating the number of CD44⁺ CK5⁺ cancer cells;
    wherein the presence of CD44⁺ CK5⁺ cancer cells is indicative of the presence of TCC cancer stem cells.

2. The method of claim 1, wherein said reagents further include a reagent specific for one or more of β-catenin; signal transducer and activator of transcription 3 (Stat3); and B lymphoma Mo-MLV insertion region 1 (Bmi-1) and determining nuclear localization of said one or more of β-catenin; Stat3; or Bmi-1.

3. The method of claim 1, wherein the quantitating is performed by flow cytometry.

4. The method of claim 1, wherein the quantitating is performed by immunohistochemistry.

5. The method of claim 1, wherein the sample is a biopsy sample.

6. The method of claim 1, wherein the patient has been diagnosed as having TCC.

7. The method of claim 6, wherein the patient is undergoing treatment for TCC.

8. The method of claim 1, wherein said patient is a human.

* * * * *